United States Patent [19]
Bohman et al.

[11] Patent Number: 4,929,904
[45] Date of Patent: May 29, 1990

[54] MOISTURE SENSING APPARATUS WITH MOVABLE PROBE IN COMBINATION WITH AN AGRICULTURAL BALER HAVING A PICKUP

[75] Inventors: Carl E. Bohman; Shaun A. Seymour, both of New Holland, Pa.

[73] Assignee: Ford New Holland, Inc., New Holland, Pa.

[21] Appl. No.: 383,694

[22] Filed: Jul. 24, 1989

[51] Int. Cl.⁵ .................................... G01R 27/14
[52] U.S. Cl. ................................ 324/696; 324/694; 56/10.2; 340/684
[58] Field of Search ................. 324/65 R, 65 P, 61 R, 324/61 P, 439, 447, 446, 450, 694–696; 56/DIG. 15, 16.4, 10.2, DIG. 23, 432; 73/73; 340/684

[56] References Cited

U.S. PATENT DOCUMENTS

| | | | |
|---|---|---|---|
| 2,829,340 | 4/1958 | Lippke | 324/61 P |
| 4,253,272 | 3/1981 | Bertness | 324/61 R X |
| 4,259,829 | 4/1981 | Strubbe | 56/DIG. 15 X |
| 4,278,934 | 7/1981 | Ihara et al. | 324/61 P |
| 4,278,935 | 7/1981 | Ihara et al. | 324/61 P |
| 4,288,742 | 9/1981 | Walsh | 324/61 R |
| 4,451,781 | 5/1984 | Anderson | 324/65 R |
| 4,513,608 | 4/1985 | Cuming | 73/73 |
| 4,531,087 | 7/1985 | Larson | 324/65 P |
| 4,532,797 | 8/1985 | Yang | 73/75 |
| 4,638,291 | 1/1987 | Puscasu | 340/59 |
| 4,812,741 | 3/1989 | Stowell | 324/65 P |

Primary Examiner—Reinhard J. Eisenzopf
Assistant Examiner—Jack B. Harvey
Attorney, Agent, or Firm—Darrell F. Marquette; Frank A. Seemar; Larry W. Miller

[57] ABSTRACT

Apparatus for sensing moisture in crop material includes a probe mounted on a pickup of an agricultural baler for movement between a retracted position and an operative position. The probe has a pair of fingers arranged in a spaced apart relationship so that crop material picked up by the baler bridges the space between the fingers when the probe is in the operative position thus creating a signal path between the fingers. The moisture sensing apparatus also includes a cam roller carried on the pickup to move the probe from its retracted position to its operative position, and a computer connected to the probe to measure the conductance level of the crop material creating the signal path.

10 Claims, 5 Drawing Sheets

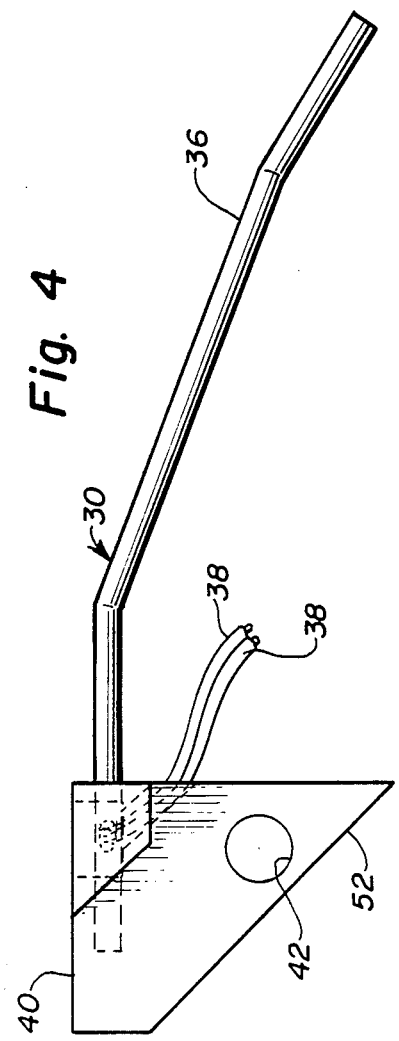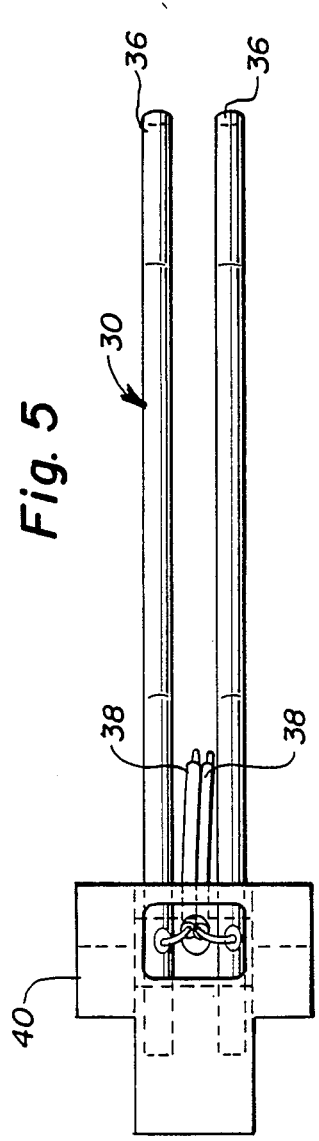

MOISTURE SENSING APPARATUS WITH MOVABLE PROBE IN COMBINATION WITH AN AGRICULTURAL BALER HAVING A PICKUP

BACKGROUND OF THE INVENTION

This invention relates generally to agricultural balers and, in particular, to moisture sensing apparatus for use on such balers.

When baling crop material with an agricultural baler, it is important for the operator to have some knowledge of the moisture content of the crop material being baled. Moisture sensors such as disclosed in U.S. Pat. No. 4,451,781 granted May 29, 1984, to J. W. Anderson have been located in the bale case of the baler. This location of the moisture sensor has a drawback in that it provides a measure of moisture content after the material has been formed into a bale and after the application of a preservative. Furthermore, preservatives with significant water content cause errors in moisture sensing at this location.

SUMMARY OF THE INVENTION

It is an object of the present invention to provide moisture sensing apparatus which measures moisture content of crop material before it has been formed into a bale and before the application of a preservative thereto.

It is another object of the present invention to provide moisture sensing apparatus which is mounted on a pickup of an agricultural baler.

Accordingly, the present invention provides, in combination with an agricultural baler having a pickup with a plurality of tines for picking up crop material, moisture sensing apparatus comprising a probe mounted on the pickup for movement between a retracted position and an operative position. The apparatus also includes means for moving the probe from the retracted position to the operative position and into the crop material picked up by the tines. In its preferred embodiment, the probe comprises a pair of fingers arranged in a spaced apart relationship so that crop material picked up by the tines bridges the space between the fingers when the probe is in the operative position thereby creating a signal path between the fingers.

The moisture sensing apparatus of the present invention also comprises means for measuring the conductance level of the crop material creating the signal path between the fingers of the probe. Furthermore, the moisture sensing apparatus comprises means for indicating the moisture content of the crop material based on the conductance level as measured by the means for measuring.

DESCRIPTION OF THE DRAWINGS

FIGS. 4 and 5 are side elevation and top plan views, respectively, of the probe of the moisture sensing apparatus of the present invention.

DESCRIPTION OF THE PREFERRED EMBODIMENT

Figure 1:
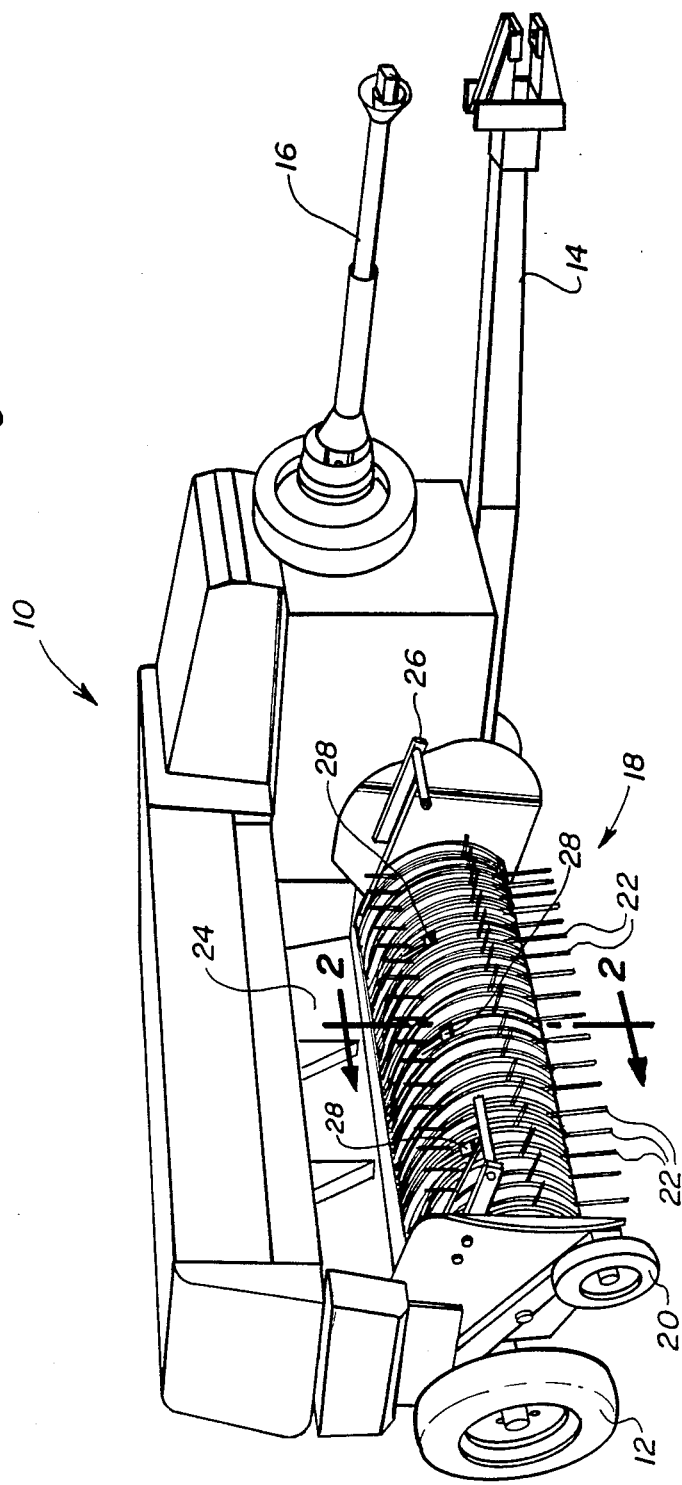
FIG. 1 is a front perspective view of an agricultural baler incorporating a moisture sensing apparatus according to the present invention.

Referring to FIG. 1, an agricultural baler 10 is supported by a pair of wheels 12 and has a tongue 14 for connection to a tractor (not shown). A drive shaft 16 on the baler 10 is adapted for connection to the PTO of the tractor in conventional manner. Baler 10 also includes a pickup 18 supported by a wheel 20 and having a plurality of tines 22 with the tips thereof movable in a preselected path P shown in FIG. 2 to lift crop material from the ground onto the feeder area 24 of the baler 10. A conventional windguard 26 on the pickup 18 holds crop material down into engagement with the tines 22 after being picked up.

Figure 2:
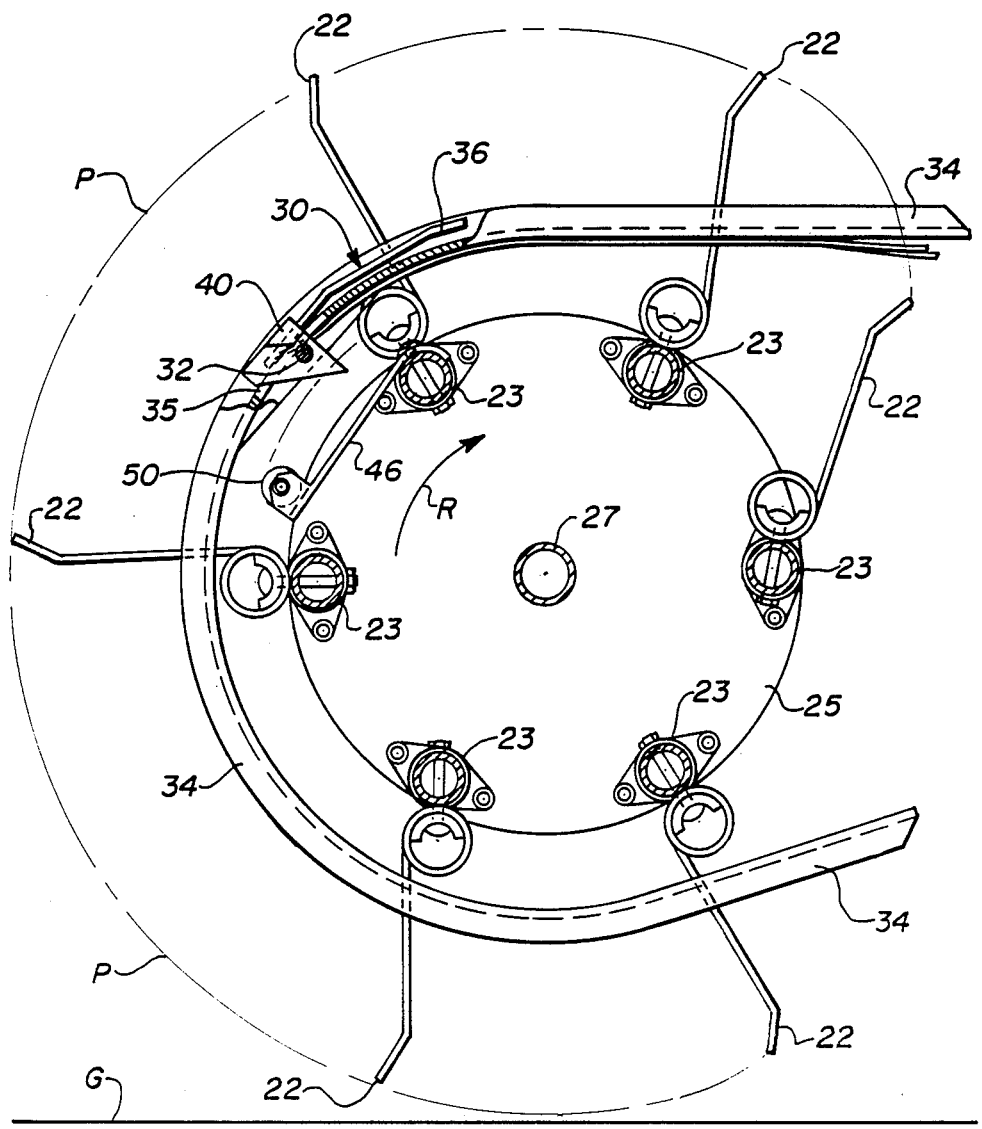
FIG. 2 is an enlarged view of a pickup, partly in section, taken along lines 2—2 in FIG. 1 illustrating the moisture sensing apparatus of the present invention.
Figure 3:
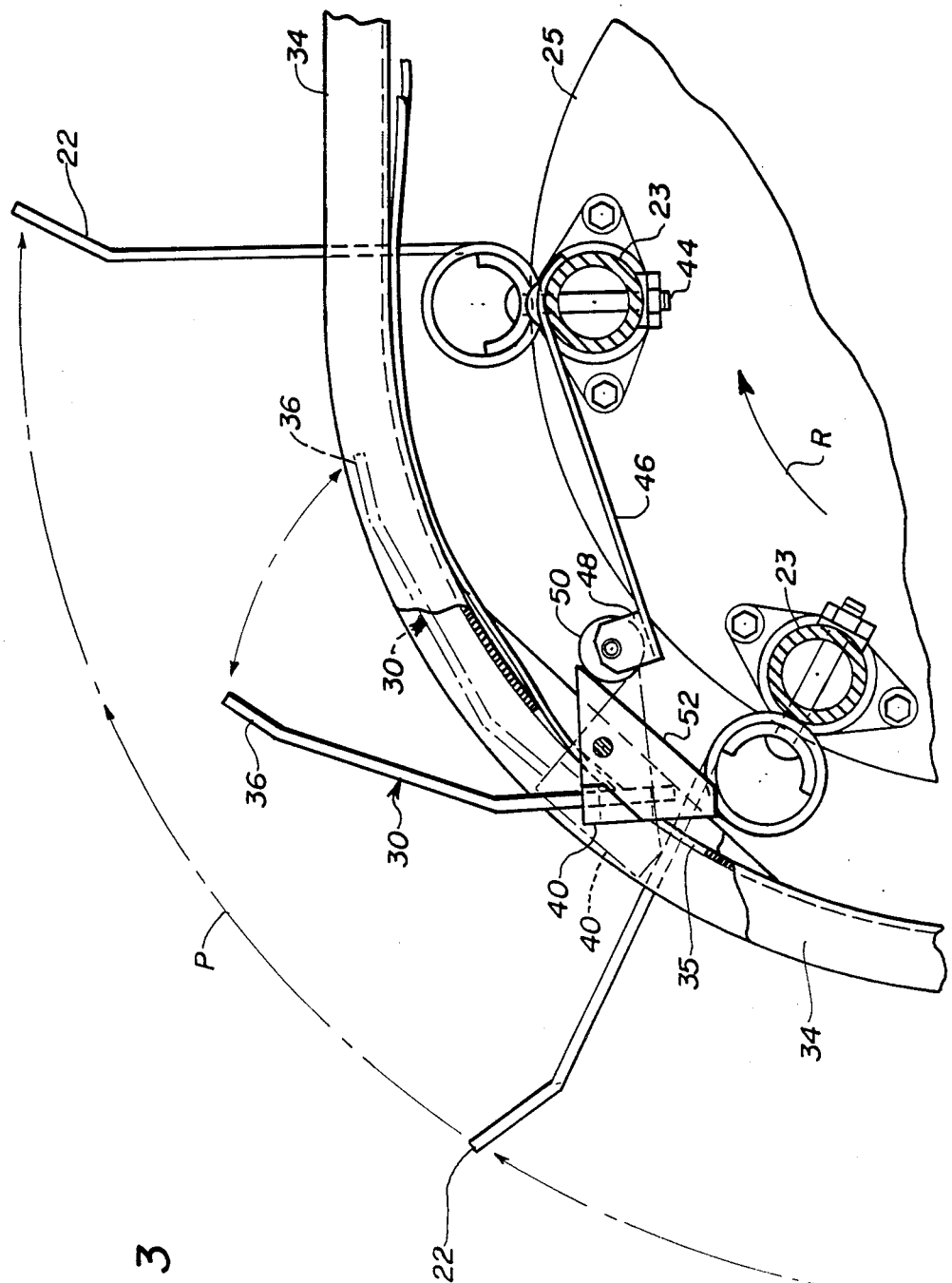
FIG. 3 is a further enlarged view of a portion of the pickup shown in FIG. 1 illustrating the relative movement of a probe of the moisture sensing apparatus of the present invention.

According to the present invention, moisture sensing apparatus 28 is mounted on the pickup 18 across the width thereof. As seen in FIGS. 2 and 3, moisture sensing apparatus 28 includes one or more probes 30 pivoted on pins 32 which are carried on stripper blades 34 of the pickup 18 for relative movement between a retracted position shown in full lines in FIG. 2 and an operative position shown in full lines in FIG. 3. Probes 30 are each comprised of a pair of fingers 36, 36 rigidly mounted in a block 40. Preferably, the fingers 36, 36 are formed of a suitable metallic material such as stainless steel, while the blocks 40 are formed of an electrically insulating material which is nonabsorptive. Electrical wires 38, 38 are connected to the respective fingers 36, 36 of each probe 30.

It will be understood that pickup 18 includes a series of stripper blades 34 arranged side by side as seen in FIG. 1. The stripper blades 34a on which the pins 32 are carried each have a cutout 35 provided therein to accommodate a block 40 that forms part of a probe 30. The blocks 40 have holes 42 for receiving the pins 32. The fingers 36, 36 of the probes 30 are properly contoured, as viewed in side elevation in FIG. 4, so that they lie below the upper edges of the side flanges of the stripper blades 34a when the probes 30 are in their retracted position.

Referring to FIG. 2, it will be seen that pickup tines 22 are attached in conventional manner to bars 23 that are fastened between side plates 25. The bars 23 are arranged parallel to a central shaft 27 of the pickup 18. Also attached to one of the bars 23 by bolts 44 are spring arms 46, each of which has a pair of ears 48 at the free end thereof rotatably supporting a cam roller 50. The blocks 40 of the probes 30 each have a cam surface 52 disposed for engagement with an associated cam roller 50.

During operation of the baler 10, pickup tines 22 rotate in direction R as indicated in FIGS. 2 and 3 to lift crop material from the ground G into the feeder area 24 of the baler 10. The bars 23 revolve in a circular path about the axis of the central shaft 27 while the tips of the tines 22 follow the path P. When the bar 23a on which the spring arms 46 and the rollers 50 are carried reaches the point in its circular path shown in FIG. 3, the probes 30 will have been moved from their retracted position to their operative position. This movement of the probes 30 is effected by the rollers 50 contacting the cam surfaces 52 of the blocks 40, thereby causing counterclockwise rotation of the blocks 40 as viewed in FIG. 3. As the probes 30 move away from their retracted positions, the fingers 36 are moved into the path of the crop material that is being lifted from the ground G into the feeder area 24 of the baler 10 by the tines 22. Crop material is compressed between the fingers 36 and the windguard 26 to establish reliable contact with the fingers 36.

The crop material contacting the fingers 36 of each probe 30 bridges the space between the fingers 36 thereby creating a signal path therebetween. As the moisture content of the crop material varies, the conductance level of this signal path will also vary. For example, crop material with a high moisture content will generate a high conductance level while crop material with a low moisture content will generate a low conductance level. Therefore, the conductance level generated by the crop material provides an accurate indication of its moisture content.

Figure 6:
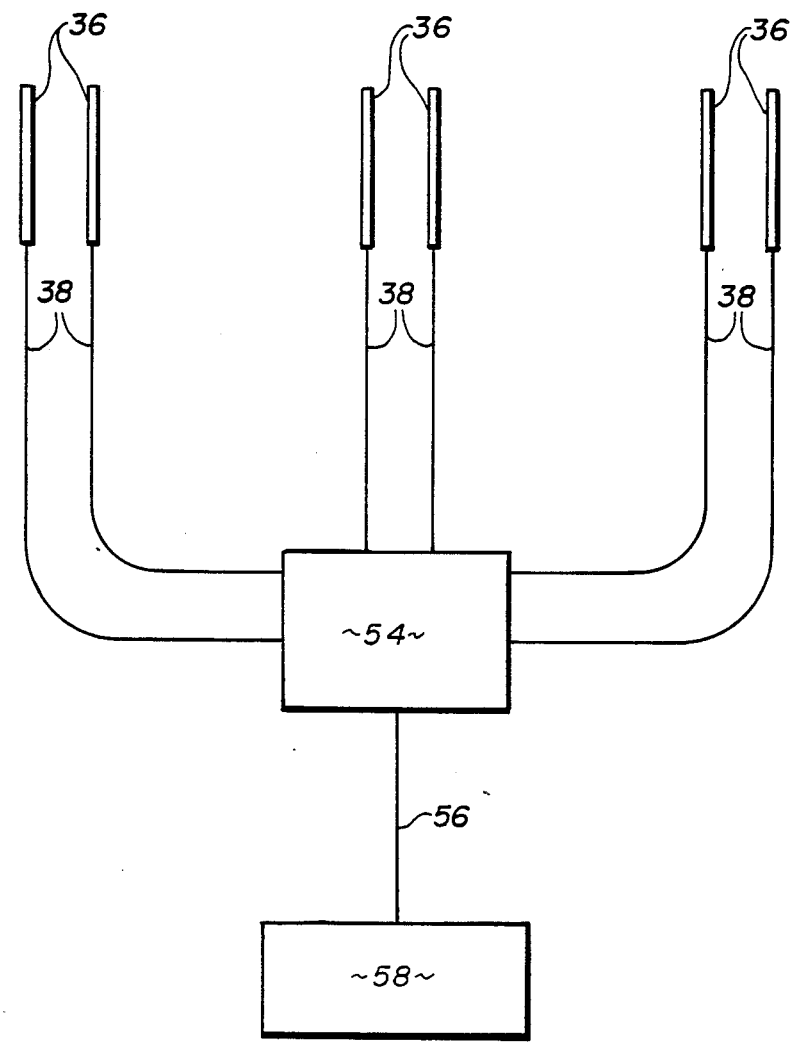
FIG. 6 is a schematic illustration of a system incorporating the moisture sensing apparatus of the present invention.

Referring to FIG. 6, it will be understood that the fingers 36 of the probes 30 are connected by the respective electrical wires 38 to an electronic circuit such as a computer 54 which measures the conductance level of the crop material and then determines its moisture content. The computer 54 is connected by electrical wiring 56 to a visual indicator panel 58 on which the moisture content of the crop material is indicated. Preferably, the computer 54 will be programmed to take a sample measurement of the conductance level of the crop material bridging the space between the fingers 36 of the probes 30 only when the probes 30 are in their operative positions shown in full lines in FIG. 3.

What is claimed is:

1. In combination with an agricultural baler having a pickup including a plurality of tines movable in a preselected path for picking up crop material and a bale case in which crop material is formed into bales, moisture sensing apparatus comprising:
   a probe mounted on said pickup for movement between a retracted position and an operative position in order to check the moisture content of the crop material being picked up by said tines before it enters said bale case; and
   means actuated when said times move in said preselected path for moving said probe from said retracted position to said operative position and into the crop material picked up by said tines.

2. The apparatus of claim 1, wherein said probe comprises a pair of fingers arranged in a spaced apart relationship so that crop material picked up by said tines bridges the space between said fingers when said probe is in said operative position, thereby creating a signal path between said fingers.

3. The apparatus of claim 2, further comprising means for measuring the conductance level of the crop material creating said signal path.

4. The apparatus of claim 3, wherein said means for measuring comprises an electronic circuit connected to said probe.

5. The apparatus of claim 3, further comprising means connected to said measuring means for indicating the moisture content of the crop material based on the conductance level as measured by said measuring means.

6. The apparatus of claim 2, wherein said fingers are rigidly mounted in a block which is pivotally mounted on said pickup.

7. The apparatus of claim 6, wherein said means for moving comprises cam means carried on said pickup and arranged for engagement with a cam surface on said block to thereby move said probe from said retracted position to said operative position.

8. The apparatus of claim 7, wherein said cam means comprises a cam roller carried on a spring arm which is attached to one of a plurality of bars, said bars extending transversely of said pickup and carrying said tines.

9. The apparatus of claim 8, wherein said block is pivoted on a pin which is carried on said pickup.

10. An agricultural baler comprising:
   a pickup including a plurality of tines movable in a preselected path for picking up crop material;
   a bale case in which crop material is formed into bales;
   a probe mounted on said pickup for movement between a retracted position and an operative position in order to check the moisture content of the crop material being picked up by said tines before it enters said base case; and
   means actuated when said tines move in said preselected path for moving said probe from said retracted position to said operative position and into the crop material being picked up by said tines.

* * * * *